(12) United States Patent
Steenbakkers (10) Patent No.: US 6,392,020 B1
(45) Date of Patent: May 21, 2002

(54) MONOCLONAL ANTIBODY TO THE CLONOTYPIC STRUCTURE OF A T-CELL RECEPTOR, A PHARMACEUTICAL COMPOSTION AND A DIAGNOSTIC REAGENT COMPRISING THE SAME

(75) Inventor: Petrus Gerardus Antonius Steenbakkers, Erp (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/405,745

(22) Filed: Sep. 27, 1999

Related U.S. Application Data (62) Division of application No. 08/985,898, filed on Dec. 5, 1997, now Pat. No. 6,020,170.

(30) Foreign Application Priority Data

Dec. 6, 1996 (EP) .............................................. 96203465
Jun. 27, 1997 (EP) .............................................. 97201972

(51) Int. Cl.$^7$ ...................... C12E 21/08; A61K 39/395; G01N 33/53

(52) U.S. Cl. .............................. 530/388.75; 530/388.1; 530/388.22; 424/141.1; 424/143.1; 424/154.1; 436/548

(58) Field of Search ......................... 530/388.75, 388.1, 530/388.22; 424/141.1, 143.1, 154.1; 436/548

(56) References Cited

U.S. PATENT DOCUMENTS

| | | | |
|---|---|---|---|
| 5,162,223 A | | 11/1992 | Brennans et al. |
| 5,223,426 A | | 6/1993 | Skibbens et al. |
| 5,766,947 A | * | 6/1998 | Rittershaus et al. ........ 435/334 |
| 5,980,892 A | * | 11/1999 | Skibbens et al. ........ 424/144.1 |
| 6,015,884 A | * | 1/2000 | Schneck et al. ......... 530/387.3 |
| 6,048,526 A | * | 4/2000 | Skibbens et al. ........ 424/144.1 |

FOREIGN PATENT DOCUMENTS

EP  488470 A  6/1992

OTHER PUBLICATIONS

Cantagrel et al. Rev. Rhumat. Malad. Osteo–Articul. 60: S45–S52, 1993.*
Kanagawa et al. J. Immunol. Methods 110: 169–178, 1988.*
Hakala et al. J. Biol. Chem. 268: 25803–25810, 1993.*
Texier et al. J. Immunol. 148: 439–444, 1992.*
Owhashi et al. J. Exp. Med. 168:2153–2164, 1988.*
Yoshino et al. Eur. J. Immunol. 20: 2805–2808, 1990.*
Reinsmoen et al. In: Advances in Gene Technology: Molecular Biology of the Immune System, vol. 2, (Ed) Streilein et al. 17th Miami Winter Symposium, Miami, Cambridge University Press, Feb. 11–15, 1985, pp. 275–276.*
Callan et al. PNAS 90 (22): 10454–10458, abstract, 1993.*
P. Steenbakkers et al., *Journal of Immunological Methods*, 152:1:69–77, 1992.
P. Steenbakkers et al., *Molecular Biology Reports*, 19:2:125–134, 1994.
M. Glasky et al., *Hybridoma*, 8:4:377–389, 1989.
Steenbakkers et al., *J. Immunol. Methods*, 163:33–40, 1993.
Steenbakkers et al., *Hum. Antibody. Hybridoma*, 4:166–173, 1993.
Vartdal et al., *Transplantation*, 43:366–371, 1987.
Kvalheim et al., *Cancer Res.*, 47:849–851, 1987.
Ossendorp et al., *J. Immunol. Methods*, 120:191–200, 1989.
Horton et al., *J. Immunol. Methods*, 124:225:230, 1989.

* cited by examiner

*Primary Examiner*—S. Devi
(74) *Attorney, Agent, or Firm*—Rothwell, Figg, Ernst & Manbeck, p.c.

(57) ABSTRACT

The present invention relates to an efficient method of producing monoclonal antibodies against surface antigens of cells and viruses. The method accommodates for antigens which are present in only relatively small amounts, or antigens of which only very small amounts are available or antigens which easily lose their in vivo conformation. Thus the method according to the invention comprises a series of steps, comprising a step in which B-cells from a mammal injected with surface antigen-comprising material are enriched with respect to the relative number of specific B-cells and a step which comprises a small-scale fusion technique.

9 Claims, 6 Drawing Sheets

Figure 1: Identification of H.243 T-cell surface molecules immunoprecipitated by MAb directed against H.243.

Figure 2: Anti-clonotype MAb recognize TCRαβ in Western blotting.

Figure 3: Immobilized anti-TCR MAb stimulate proliferation of human T-cell clone H.243.

A

B

Figure 4: Pre-incubation with anti-TCR MAb inhibit or block antigen-driven proliferation of human T-cell clone H.243.

Figure 5: Anti-clonotype MAb induce anergy in human Th1-clone H.243.

Figure 6: Anergic H.243 T cells suppress the response of non-anergic H.243 T cells.

MONOCLONAL ANTIBODY TO THE CLONOTYPIC STRUCTURE OF A T-CELL RECEPTOR, A PHARMACEUTICAL COMPOSTION AND A DIAGNOSTIC REAGENT COMPRISING THE SAME

CROSS-REFERENCE TO RELATED APPLICATION

The present application is a divisional of U.S. application Ser. No. 08/985,898, filed on Dec. 5, 1997 (now U.S. Pat. No. 6,020,170), incorporated herein by reference in its entirety.

FIELD OF THE INVENTION

The present invention relates to a method of preparing a monoclonal antibody against a surface antigen, and in particular such a surface antigen which constitutes only an insignificant amount of the total antigen injected in a mammal and a surface antigen which easily loses its in vivo conformation. The problem of an insignificant amount of antigen relative to the total amount of antigen for example sets in when the antigen material used to inject a mammal is derived from another mammalian species.

BACKGROUND OF THE INVENTION

The problems associated with the antigens specified above become clear when, for example, it is desired to make monoclonal antibodies against the specificity determining part of a T-cell receptor (TCR). Such (monoclonal) antibodies are known as anti-clonotype antibodies as they recognize the antigen-specific part (or clonotype structure) of a T-cell receptor of one particular T-cell clone. While (murine) monoclonal anti-clonotype antibodies against murine T-cell receptors (TCR) have been reported only occasionally, there are even less (murine) monoclonal anti-clonotype antibodies known against human T-cell receptors. T-cells are hard to culture, making it difficult to obtain and purify a sufficient amount of antigen, i.e. T-cell receptor protein. This in turn makes it difficult to obtain an immune response and also makes screening difficult. In one of the few cases where a monoclonal anti-clonotype antibody is available against a human TCR, these problems did not arise because the antigen was present on Jurkat leukaemia cells (ref. 1). As leukaemia cells can be cultured in unlimited amounts, the problem of a shortage of antigen did not arise. Therefore, until now no method was available to prepare monoclonal antibodies against rare and/or very unstable antigens without having to screen unfavourably large numbers of hybridoma clones.

SUMMARY OF THE INVENTION

The object of the present invention is to provide a method of preparing a monoclonal antibody against a cell surface antigen under unfavourable circumstances as described above, said method dramatically reducing the number of hybridoma clones to be screened, rendering the method according to the invention more efficient or even successful where methods according to the state of the art fail.

To this end the method according to the invention comprises the steps of 1) injecting a mammal with cell surface antigen-comprising material, said material being chosen from the group consisting of i) whole cells and ii) a membrane fraction obtained by treating whole cells;
2) isolating a B-cells-containing cell fraction from the spleen of said mammal;
3) enriching said cell fraction obtained in step 2 in B-cells specific for said cell surface antigen by contacting the cell fraction with carrier-bound material of cells related to said whole cells, said carrier-bound related material of cells lacking said cell surface antigen, and separating B-cells bound to carrier-bound material of related cells from the enriched unbound B-cells-containing cell fraction to be used in the next step;
4) subjecting the enriched B-cells-containing cell fraction obtained in the previous step to limiting dilution followed by clonal expansion;
5) selecting a B-cell clone and immortalising said selected B-cell clone using a small-scale fusion technique; and
6) selecting and cloning a hybridoma capable of producing antibodies which specifically bind said cell surface antigen, followed by isolating a monoclonal antibody-comprising fraction from supernatant of said hybridoma.

For the purpose of keeping the description and the claims readable and intelligible, here the term cell is used not only to indicate mammalian cells but also viruses, and in particular membrane-comprising viruses.

The term carrier-bound material of cells encompasses intact or whole cells (and viruses), membrane fractions of said intact whole cells (and viruses), or substantially purified surface-antigens or complexes thereof.

Unless specified otherwise, the term whole cell refers to cells having the surface antigen of interest. The term related cells refers to cells which preferably differ only in that they lack the surface-antigen of interest, or more specifically at least lack the immunological determinant against which it is desired to obtain a monoclonal antibody.

Surprisingly it proved to be possible to enrich the cell fraction in B-cells specific for the cell surface antigen without the use of cell surface antigen by contacting the isolated B-cells-containing cell fraction with material of cells from the same species as the cell surface antigen-comprising material was derived of but lacking the cell surface antigen. In other words, by contacting the B-cells with irrelevant related cells or cell material and removing bound B-cells an enrichment was achieved.

Thus it is possible to prepare a monoclonal antibody against a minor cell surface antigen, even if said cell surface antigen suffers from conformational instability.

European patent EP 0 488 470 and ref. 3, which is based on this European patent, describe a method in which I) a mammal is injected with an antigen, II) a B-cells-containing fraction is isolated, III) B-cells specific for the antigen are selected, IV) the enriched fraction is subjected to clonal expansion and after V) selecting a B-cell clone and immortalisation using a small-scale fusion technique a VI) hybridoma is selected and cloned followed by isolation of a monoclonal antibody comprising fraction. In step III the B-cells are selected by binding them on an antigen coated plastic surface or by resetting them with antigen coated paramagnetic beads. The non-specific B-cells are removed by washing. Thus, apart from other differences, this method relies on the ample availability and use of antigen—during the selection 2 $\mu$g/ml antigen is used to coat plates with antigen—, whereas the present invention solves the problem for a case in which antigen is available in very limited amounts and even highly impure.

A preferred embodiment is characterized in that the mammal injected with surface antigen is of a different species than the mammalian species from which the surface antigen originates.

The method according to the present invention is very suitable for preparing monoclonal antibodies when many antigens capable of eliciting an immuneresponse are present.

This situation exists in particular when the surface antigen has a constant section and a variable section, wherein at least a part of said variable section defines a specificity determining part of said surface antigen.

According to a preferred embodiment receptor molecule-comprising material is used as the cell surface antigen-comprising material.

The method according to the invention is particularly suitable for preparing monoclonal antibodies against the specificity determining part of a receptor molecule. The specificity determining part of the receptor molecule is only a minor part of the receptor molecule, which in itself is a minor constituent of all the molecules—and thus antigens—on the surface of a cell.

A preferred target according to the invention is a T-cell clone, which T-cell clone is used to prepare the receptor molecule-comprising material.

A T-cell may be used as a whole cell, or used for the preparation of a membrane fraction thereof. Thus, in the former case the term prepare may, here, relate to the mere isolation of a T-cell or resuspending in a different medium.

According to preferred embodiments the membrane fraction in step 1 is obtained by mechanical treatment of the whole cells, and the cell surface antigen-comprising material is injected in the mammal in the absence of an adjuvant.

Both measures help to prevent loss of the in vivo conformation of the surface antigen.

Furthermore, the enriched B-cells-containing cell fraction is preferably further enriched (step 3) by contacting the cell fraction with carrier-bound cell surface antigen comprising material chosen from the group of i) whole cells, ii) a membrane fraction obtained from said whole cells, and iii) substantially purified cell surface antigen, and subsequently separating B-cells not bound to said carrier-bound material from B-cells bound to said carrier-bound material, said B-cells bound to said carrier-bound material comprising the further enriched cell fraction.

This further enrichment can be designated as a positive selection technique, selecting specifically specific B-cells. Thus, though hardly any antigen is available, further enrichment could be achieved.

According to a preferred embodiment paramagnetic beads are advantageously used as the carrier.

The use of paramagnetic beads during the enrichment facilitates the separation of wanted and unwanted B-cells.

An insignificant amount of antigen also presents a problem during screening. According to a preferred embodiment, the selection in at least one of the steps 5 and 6 is conducted using an agglutination assay wherein supernatant of the B-cell clone is contacted with a carrier coated with antibodies capable of binding antibodies of the species of the injected mammal used in step 1 and whole cells bearing the cell surface antigen, and agglutination is detected.

Simply mixing B-cell culture supernatant, whole cells and a carrier coated with antibodies capable of binding antibodies of the mammalian species used in step 1, allows for a very sensitive and rapid detection of suitable clones while washing is not required.

Advantageously related cells (whole cells which lack the surface antigen) are used as controls.

This allows for the rejection of false-positive clones, and saves time by avoiding superfluous small-scale fusions.

According to a preferred embodiment of the method according to the invention, the selected B-cell clone in step 5 is mixed with myeloma cells and subjected to mini-electrofusion.

Mini-electrofusion allows for the efficient fusion of very small numbers (e.g. hundreds) of cells.

The invention also relates to a pharmaceutical composition comprising a monoclonal antibody prepared according to the invention admixed with a suitable excipient.

Furthermore the present invention relates to a monoclonal antibody reactive with the clonotypic structure of a T-cell receptor.

Such monoclonal antibody can be used for diagnostic purposes as well as for the preparation of a pharmaceutical composition.

More specifically the T-cell receptor is a T-cell receptor associated with an auto-immune disease, and in particular rheumatoid arthritis.

Preferably the monoclonal antibody is reactive with the T-cell receptor of a HC gp-39 reactive T-cell clone, and in particular with the T-cell clone H.243 (ECACC accession No. 96103122).

Specific examples of suitable monoclonal antibodies are those produced by a hybridoma chosen from the group consisting of TCR 69 (ECACC accession No. 96103118), TCR 70 (ECACC accession No. 96103119), TCR 72 (ECACC accession No. 96103120) and TCR 83 (ECACC accession No. 96103121).

The above deposits were made under the Budapest Treaty on Oct. 31, 1996 with the European Collection of Cell Cultures, Centre for Applied Microbiology and Research, Porton Down, Salisbury SP4 0J6, United Kingdom.

As indicated above, the invention also relates to pharmaceutical composition comprising a monoclonal antibody according to the invention admixed with a suitable excipient, suitable for the treatment of rheumatoid arthritis.

Finally the invention relates to the diagnostic use of a monoclonal antibody chosen from the group consisting of a monoclonal antibody prepared using the method according to the invention and a monoclonal antibody according to the invention. Also a diagnostic reagent comprising the antibody is an embodiment of the invention.

Now the invention will be explained in further detail with reference to the following example, said example showing the best mode of carrying out the invention applied to the preparation of a murine monoclonal antibody specific for a clonotype of a human T-cell receptor.

BRIEF DESCRIPTION OF THE DRAWINGS

Each value represents the mean counts per 5 min of quadruplicate cultures +/– standard deviation.

DETAILED DESCRIPTION OF THE INVENTION

EXAMPLES

Materials and Methods
Reagents

Culture medium: DMEM/HAM's F12 (Gibco cat. no. 32500) supplemented with 2500 mg/l sodium bicarbonate, 2.3 mg/l 2-mercaptoethanol, 55 mg/l sodium pyruvate, 1.22 mg/l ethanolamine, 360 mg/l L-glutamine, $4.5\times10^{-4}$ mg/l sodium selenite, 62.5 mg/l sodium penicillin and 62.5 mg/l streptomycin sulphate. In fusion experiments, the medium was further supplemented with 13.61 mg/l hypoxanthine and 3.83 mg/l thymidine. This medium is referred to as DMEM/HAM's F12/HT. Selection of hybridomas was performed in DMEM/HAM's F12/HT supplemented with 1% (v/v) of IL-6 containing supernatant of a human bladder carcinoma cell line T24 (T24CM) and 0.4 $\mu$M aminopterin.

Fusion medium: 280 mM inositol, 0.1 mM calcium acetate, 0.5 mM magnesium acetate and 1 mM histidine; specific resistance: $1.11\cdot10^4$ $\Omega\cdot$cm. Ingredients were dissolved in Milli-Q water and subsequently the conductivity was adjusted to 90 $\mu$S/cm with Milli-Q water or a solution containing 1 mM calcium acetate and 5 mM magnesium acetate.
Cell Cultures T-cell clone H.243 was derived from a patient suffering from rheumatoid arthritis. This Th1-like T-cell clone recognizes epitope RSFTLASSETGVG (SEQ ID NO: 1) from Human Cartilage gp-39 (HC gp-39) in the context of DRB1*0401 (belongs to MHC class II). The TCR of this clone is characterized as V$\alpha$8 and V$\beta$9 positive. Cells were routinely cultured in DMEM/HAM's F12 supplemented with 10% FCS, 20 U/ml IL-2, 5 U/ml IL-4 and periodically restimulated with antigen and histocompatible Antigen Presenting Cells (APC) or with phytohemagglutinin (PHA) and feeder cells. For proliferation assays Foetal Calf Serum (FCS) was replaced by Normal Human Serum (NHS).
Preparation of T-cell Lysate and Loading Beads with TCR/CD3 Complexes Ten to fourteen days after restimulation, T-cells were washed with PBS and solubilized by incubating (30 min, 0° C.) them at a concentration of $10^8$ cells/ml in extraction buffer according to Oettgen et al. (ref. 2) (10 mM triethanolamine, 150 mM NaCl, 1 mM Na$_2$EDTA, 1% digitonin, 10 $\mu$g/ml leupeptin, 10 $\mu$g/nl aprotinin, 1 $\mu$g/ml pepstatin, 1 mM Pefabloc® AEBSF and 1,8 mg/ml iodoacetamine pH 7.8). The mild detergent digitonin allows extraction of intact TCR/CD3 complexes. Nuclear and cellular debris was removed by centrifugation at 16,000 g for 15 min. at 4° C. and the supernatant was stored in aliquotes at –20° C. until use for selection of B-cells or immunoprecipitation.

For selection of specific B-cells, paramagnetic beads were loaded with TCR/CD3 complexes.

Briefly, 100 $\mu$l Sheep anti-mouse Ig coupled paramagnetic beads (SAM-beads; Dynabeads® 110.02) were incubated (overnight, 4° C.) with 22 $\mu$g anti-CD3, OKT3, in PBS with 0.1% BSA. After washing the beads with PBS/BSA, $1.4\times10^8$ cell equivalents of T-cell lysate and an equal volume (1.4 ml) PBS/BSA with 1% normal mouse serum were added. The latter was added to prevent binding of B-cells to free SAM binding sites on the beads. The bead suspension was incubated for 2 o 4 hours at 4° C. and washed with PBS/BSA before use.
Immunization Six-week old female BALB/C mice were immunized at 3- to 7 week intervals with either $5\times10^6$ whole T-cells (invention) or paramagnetic beads loaded with TCR/CD3 complexes of $5\times10^7$ cell equivalents (control experiment). Different routes of administration were used as indicated in Table I. In case adjuvant was used (control experiment), the first injection was performed with complete Freund's adjuvant, subsequent injections with incomplete Freund's adjuvant and the final boost without adjuvant.
Generation of Anti-clonotype MAb Female BALB/C mice, 6 weeks of age, were injected intraperitoneally 4 times at 3- to 7-week intervals, each time with $5\times10^6$ resting T-cells in PBS. Five days after the final injection, mice were sacrificed and erythrocyte and monocyte-depleted spleen cell populations were prepared as described previously (refs. 23, 24). This results in a cell fraction enriched in B-cells, but does not result in the enrichment of B-cells specific for said cell surface antigen with respect to other non-specific B-cells according to step 2 of the present invention.

To preclear these spleen cell populations for B-cells reactive to human CD3 or the constant region of TCR$\alpha\beta$, approximately $3\times10^7$ cells were incubated twice with 20 $\mu$l SAM beads loaded with TCR/CD3 complexes of an irrelevant T-cell clone (V$\alpha$3.V$\beta$14 positive T-cell clone, SCRO.08A, but any other irrelevant T-cell will do). Subsequently, B-cells specific for the variable region of the TCR were selected by incubating the resulting cell suspension with SAM beads loaded with TCR/CD3 complexes of the T-cell clone of interest (H.243). Each incubation was performed for 90 min. at room temperature in DMEM/

HAM's F12 supplemented with 10% Calf Serum (Hyclone®) and 0.2% normal murine serum. During these incubations, the suspension was carefully homogenized every 5 min. After the final incubation, the beads were carefully washed five times with DMEM/HAM's F12, 10% Calf Serum and resuspended in the same medium.

Monoclonal antibody producing hybridomas were generated from these selected B-cells by clonal expansion and mini-electrofusion as described previously (23). Briefly, selected B-cells were mixed with T-cell supernatant (TSN) and 50,000 irradiated (2500 rad) EL-4 B5-cells at a final volume of 200 $\mu$l DMEM/HAM's F12 supplemented with 10% FCS in 96-well flat bottomed tissue culture plates. At day 8, supernatants were tested in a one-step T-cell agglutination assay as described below using either the T-cell clone of interest or an irrelevant T-cell clone. B-cell cultures producing discriminating MAb were submitted to a mini-electrofusion procedure. The contents of these B-cell cultures were mixed with $10^6$ NS-1 myeloma cells (25) and rendered serum-free by washing with DMEM/HAM's F12/HT. Then, the cells were treated with pronase solution for 3 min. and subsequently washed with fusion medium. Electrofusion was performed in a 50 $\mu$l fusion chamber by an alternating electric field of 30 s, 2 MHz, 400 V/cm followed by a square, high field pulse of 10 $\mu$s, 3 kV/cm and again an alternating electric field of 30 s, 2 MHz, 400 V/cm. Finally, the contents of the fusion chamber was transferred to 20 ml selection medium and plated into a 96-well microtiter plate. At day 8 after fusion, the cultures were examined for hybridoma growth and screened in the one-step T-cell agglutination assay again.

T-cell Agglutination Assay

Screening of hybridoma cultures for anti-T-cell antibodies and determination of cross-reactivity of MAb with other T-cells was performed in a one-step agglutination assay. Using half-area microtiter plates 50 $\mu$l of hybridoma supernatant was mixed with 20 $\mu$l bead/cell suspension containing $2\times10^5$ paramagnetic beads with covalently bound Sheep anti-Mouse Ig and $5\times10^4$ T-cells of interest in DMEM/HAM's F12. After 2 to 3 hours incubation at 37° C., agglutination was examined under a microscope by looking for aggregates of cells and beads.

Immunoprecipitation and Western Blotting

Ten to fourteen days after restimulation, T-cells were washed and cell surface proteins were labelled with biotin. Briefly, T-cells were incubated at a concentration of $5\times10^6$ cells/ml with 0.5 mg/ml ImmunoPure® sulfo-NHS-biotin in PBS for 30 min. at room temperature. Subsequently, the cells were washed again and solubilized as described above. Before use in an immunoprecipitation experiment, the cell lysate was precleared once by incubating the SAM-paramagnetic beads. Immunoprecipitation was perforemd by incubating $10^7$ cell equivalents of precleared lysate for 3–4 h with 15 $\mu$l SAM-paramagnetic beads preloaded with MAb (1 ml hybridoma supernatant). Then, immunoprecipitates were washed three times with PBS, boiled in sample buffer and submitted to SDS-PAGE on 10% gel either under reducing conditions or non-reducing conditions, using the method of Laemmli (ref. 5) and the Mini-protein II system (Biorad). Immunoblotting was performed according to Towbin et al. (ref. 6) using PVDF membranes. Non-specific binding sites were blocked by incubating the membranes with 5% skim milk in PBS supplemented with 0.5% Tween 20® polyoxyethylenesorbitan monolaurate. After washing, the blots were probed with streptavidine-alkaline phosphatase in PBS, 0.5% Tween 20® polyoxyethylenesorbitan monolaurate, 1% BSA, 1% normal goat serum for 1 h at room temperature. Finally, the blots were developed with BCIP and NBT as a chromogenic substrate. For Western blot studies, paramagnetic SAM-beads were loaded with TCR/CD3 complexes as described above using OKT3 as the immunoprecipitating antibody and normal T-cell lysate. After SDS-PAGE on a 10% PAA-gel under reducing or non-reducing conditions, the blots were incubated with 2.5 ml hybridoma supernatant. Bound antibodies were detected using alkaline phosphatase-conjugated goat anti-mouse Ig and BCIP/NBT as described above.

Antibody Mediated T-cell Proliferation

Flat-bottomed microtiter wells were coated (overnight, room temperature) with 100 $\mu$l Sheep anti-mouse Ig at 40 $\mu$g/ml in PBS. The wells were washed once and then incubated with 100 $\mu$l MAb at a concentration of 2 $\mu$g/ml in PBS for 2 h. Excess of free MAb was removed by washing and $2.5\times10^4$ resting T-cells were added in 200 $\mu$l DMEM/HAM's F12 supplemented with 10% NHS. After two days incubation at 37° C., the cells were pulsed with 0.5 $\mu$Ci[$^3$H]-thymidine and incubated for another 16 to 18 h Finally, the cells were harvested onto glass fibre filters and [$^3$H]-thymidine incorporation was measured by beta counting on a Matrix 96™ (Packard). Each variable was tested in quadruplicates.

Antibody Mediated Inhibition of Antigen-induced Proliferation

Flat-bottomed microtiter wells are inoculated with 20 $\mu$l hybridoma supernatant, $2\times10^4$ resting T-cells and $1\times10^5$ histocompatible MNC in 150 $\mu$l DMEM/HAM's F12 supplemented with 10% NHS. After 3 h incubation at 37° C., 50 $\mu$l of peptide RSFTLASSETGVG (SEQ ID NO:1) (16 $\mu$g/ml) was added to the cultures. The cultures were incubated for another two days at 37° C. and [$^3$H]-thymidine incorporation was determined as described above. Each variable was tested in quadruplicate.

Induction of Anergy using Clonotype-specific MAb

Twenty-four well culture plates were coated (overnight, room temperature) with 1 ml Sheep anti-mouse Ig at 40 $\mu$g/ml in PBS. The wells were washed once and then incubated with 1 ml MAb at a concentration of 2 $\mu$g/ml in PBS for 2 h. Excess of free MAb was removed by washing and $2\times10^6$ washed, resting T cells were added in 2 ml DMEM/HAM's F12, 10% NHS. Where indicated cyclosporin A (Sandoz, Bazel Switzerland), rIL-2, cycloheximide (Sigma, St Louis, Mo., USA) or HLA-DRB1*0401 matched APC (3000 rad irradiated) were added at the time of culture initiation. After overnight incubation, the plates were chilled on ice and the T cells were resuspended by pipetting. The cells were washed once with complete culture medium and used for a T-cell proliferation assay, cytokine analysis and FACS analysis as described below.

The antigen-specific proliferation response of T cells was assessed in flat-bottomed microwell cultures containing $2\times10^4$ T cells, $1\times10^5$ HLA-DRB1*0401 matched, irradiated (3000 rad) PBMC and variable antigen concentrations in 200 $\mu$l DMEM/HAM's F12, 10% NHS. After two days incubation at 37° C., the cells were pulsed with 0.5 $\mu$Ci $^3$H-thymidine and incubated for another 16–28 hours. Finally, the cells were harvested onto glass fiber filters and $^3$H-thymidine incorporation was measured by gas scintillation on a Matrix 96™ beta counter (Packard, Meriden, Conn., USA). Each variable was tested in triplicate.

Results

Immunisations

The immunisations using adjuvant (control experiment) did not yield any sera containing antibodies capable of discriminating between H.243 and irrelevant T-cells (Table 1; Immun. group II, III, and IV). The titer of the sera of group V were low (1:100 in the agglutination assay), whereas those of group I and II were much higher (1:1200).

Generation of Anti-clonotype MAb

Using spleen cells from group I, incubation with TCR/CD3 complexes from an irrelevant T-cell clone, here H.258, loaded paramagnetic beads resulted in many rosetted cells, indicating a successful removal of many CD3- and TCRαβ-reactive B-cells. When non-rosetted cells were submitted to a second preclear with irrelevant TCR/CD3-complexes from the same T-cell clone, hardly any rosetted cells were visible.

Microscopic examination after incubation with paramagnetic beads with the T-cell clone of interest, did not result in visible rosette formation. Given the expected frequency of specific B-cells, this is not surprising. After limiting dilution and clonal expansion 36 B-cell supernatants were found to agglutinate H.243 and not the irrelevant T-cell clone H.258 (Table II). Some B-cell supernatants were able to agglutinate both clones, indicating that they had escaped the preclear procedures.

Further, it can be deduced from Table II that the major part of the specific B-cell cultures are not clonal as also B-cells had grown out that do not react with any of the T-cells. However, this was not a problem because hybridomas from these non-specific B-cells could be selected out after mini-electrofusion. Eighteen of the specific B-cell cultures were submitted to a mini-electrofusion. Some fusions did not result in T-cell specific hybridomas and some others could not be cloned to stable cell lines. Ultimately stable hybridomas were obtained in 11 out of 18 mini-electrofusions. These 11 MAb were further characterized. The isotypes of these MAb are shown in Table III.

Specificity of MAb

To further investigate the specificity of the MAb, immunoprecipitation and T-cell agglutination tests as well as Western blots were performed.

Figure 1:
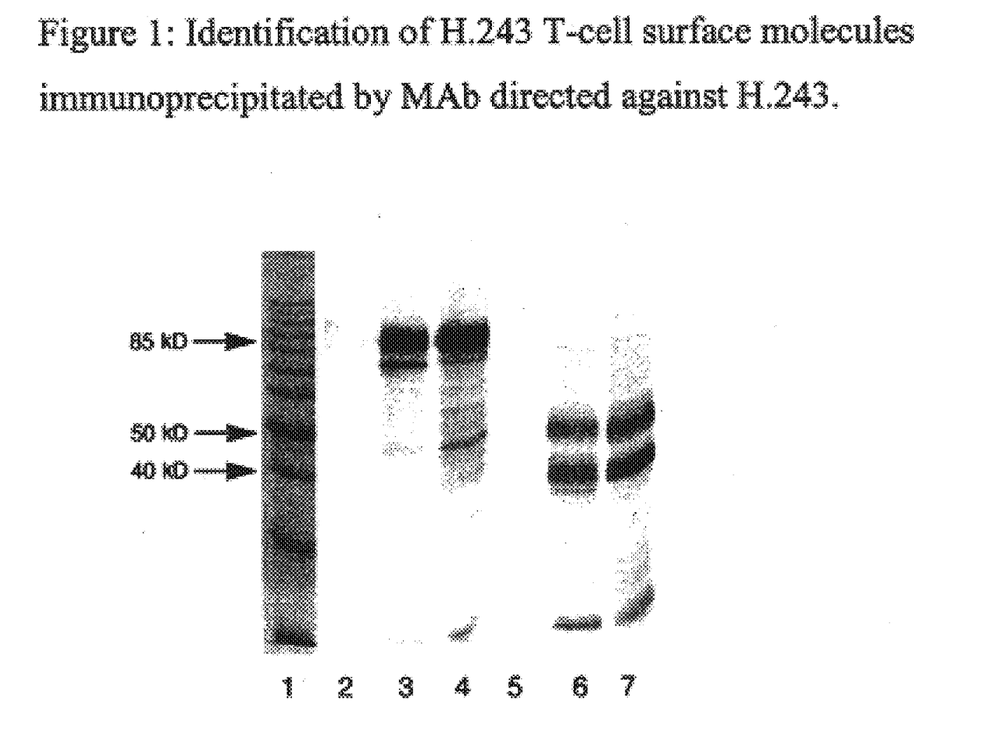
FIG. 1: Identification of H.243 T-cell surface molecules immunoprecipitated by MAb directed against H.243. SDS/PAGE was performed under non reducing conditions (lane 2, 3 and 4) or under reducing conditions (lane 5, 6 and 7) in a 10% gel. Lane 1: 10 kD ladder marker; lane 2 and 5: control MAb; lane 3 and 6: TCR 83; lane 4 and 7: anti-CD3, OKT3.

SDS/PAGE under non-reducing and denaturing conditions showed that all MAb were able to immunoprecipitate a major band of approximately 85 kD and a minor band of 21 kD from a digitonin lysate of T-cell clone H.243. This is consistent with the molecular weight of the TCRαβ-complex and of CD3 chains ε/δ, respectively. Under reducing conditions the 85 kD band dissociates into two bands of 40 and 50 kD which is consistent with molecular weight of the TCR α- and β-chains, respectively. The immunoblot of one of the anti-H.243 specific MAb is shown in FIG. 1, together with OKT3 as a positive control and an irrelevant MAb as a negative control.

Figure 2:
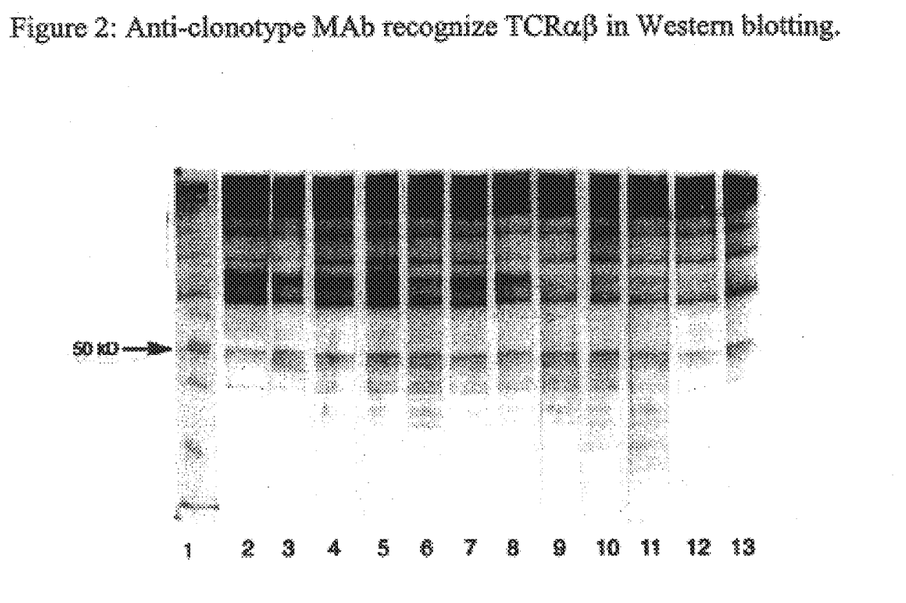
FIG. 2: Anti-clonotype MAb recognize TCR$\alpha\beta$ in Western blotting. Immunoprecipitated TCR/CD3 complexes of H.243 were resolved on a 10% SDS-PAGE gel under non reducing conditions and subsequently transferred to PVDF membranes. The membranes were incubated with MAb and finally the bound MAb were detected by using an alkaline phosphatase-conjugated goat anti-mouse Ig second antibody. Lane 1: 10 kD ladder marker, lane 2: TCR 64, lane 3: TCR 66, lane 4: TCR 69, lane 5: TCR 70, lane 6: TCR 72, lane 7: TCR 73, lane 8: TCR 76, lane 9: TCR 78, lane 10: TCR 79, lane 11: TCR 83, lane 12: control MAb, lane 13: medium control.
Figure 3:
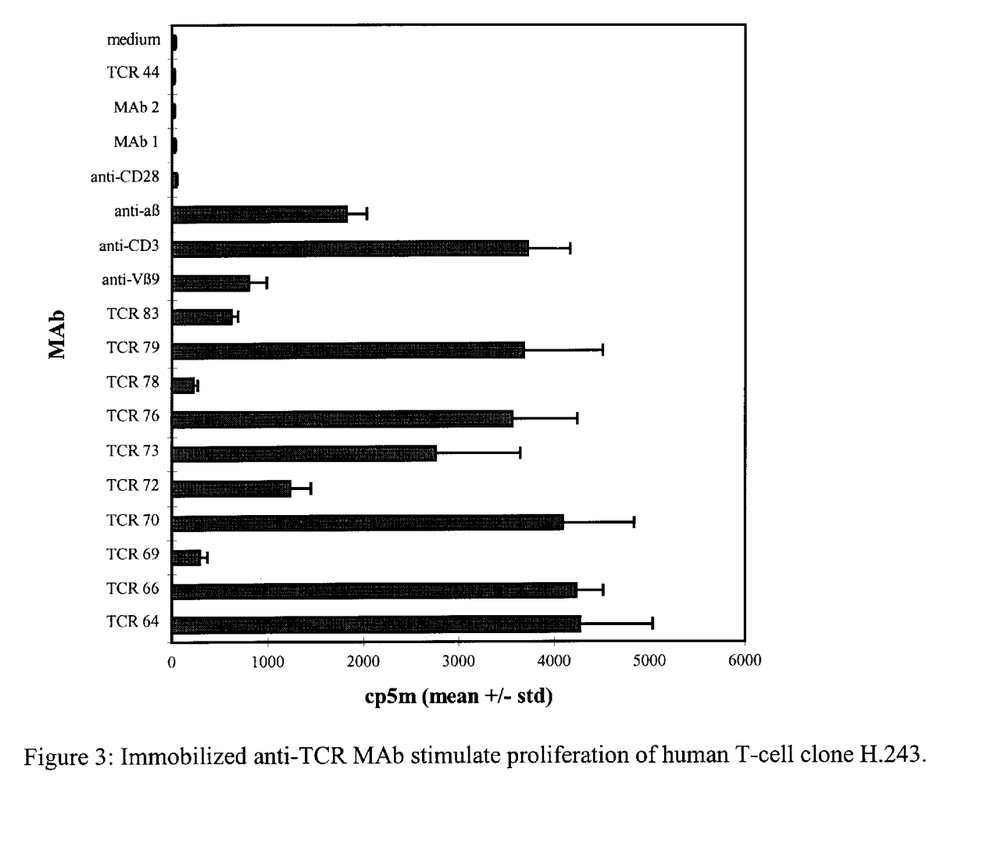
FIG. 3: Immobilized anti-TCR MAb stimulate proliferation of human T-cell clone H.243. Proliferation induced by MAb directed against H.243 (TCR 64 to TCR 83) was compared to control MAb as indicated and to TCR 44 which is an anti-clonotype MAb directed against an other TCR.

Table III shows cross-reactivity of the MAb with six Vβ9 positive T-cell clones, two Vα8 positive T-cell clones and eight other T-cell clones with different Vα and Vβ's. Antibody TCR 74 should be regarded as Vβ9 specific as it agglutinates all the Vβ9 positive T-cells and not the others. The other TCR antibodies only react with H.243 so it is very likely that these antibodies are directed against the antigen-binding part of H.243 as reaction with Vα8, Vβ9, constant region of TCRαβ, CD3 and other common T-cell surface molecules is excluded. FIG. 2 shows that antibodies from the hybridoma clones TCR 64, TCR 66, TCR 69, TCR 70, TCR 73, and TCR 76 MAb are able to stain the TCR on a non-reduced Western blot (85 kD band). The non-specific heavy bands at the top of the figure are descended from the immunoprecipitating antibodies SAM and OKT3. No staining with the anticlonotype MAb was obtained in a Western blot ran under reducing conditions (results not shown), suggesting that the MAb recognize a conformation epitope formed by the intact TCRαβ complex.

MAb Induced T-cell Proliferation

To investigate whether the MAb are able to induce proliferation of H.243 T-cells, MAb were immobilized on flat bottomed microtiter plates and incubated with T-cells. Though there are great differences between the MAb, FIG. 2 shows that all of them can induce proliferation of H.243 cells. Proliferation similar to anti-CD3 (OKT3) was obtained with TCR 64, TCR 66, TCR 70, TCR 76 and TCR 79. No proliferation was obtained with TCR 44, which is an anti-clonotype MAb for another TCR.

MAb Mediated Inhibition of Antigen-induced Proliferation of T-cells

Figure 4:
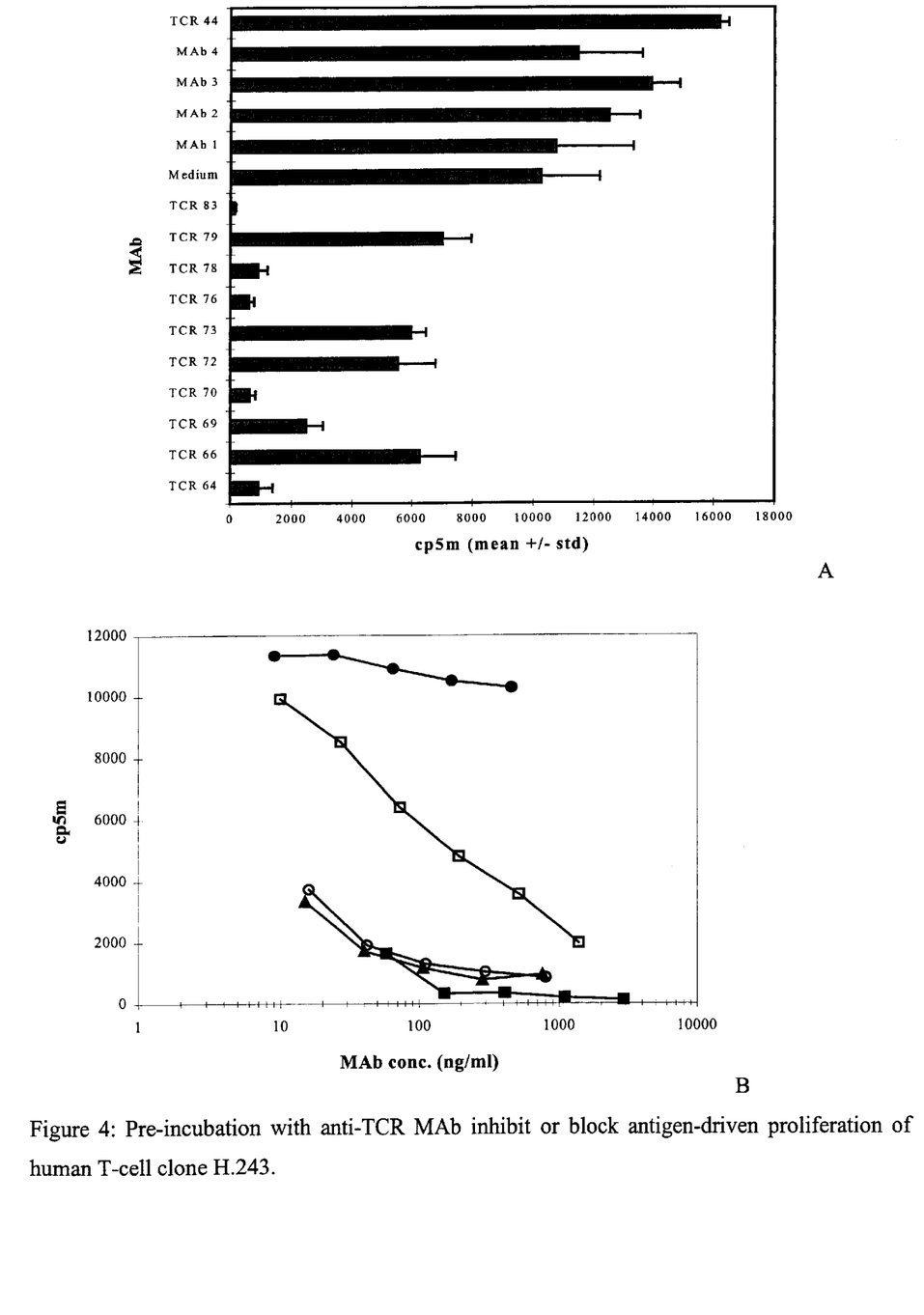
FIGS. 4A and 4B: Pre-incubation with anti-TCR MAb inhibit or block antigen-driven proliferation of human T-cell clone H.243. a) Inhibition by MAb directed against H.243 (TCR 64 to TCR 83) was compared to control MAb as indicated and to TCR 44 which is an anti-clonotype MAb directed against an other TCR. Each value represents the mean counts per 5 min of quadruplicate cultures +/– standard deviation. b) dose response curves of strong inhibiting MAb; TCR 64 (open circles), TCR 70 (closed triangles), TCR 78 (open squares), TCR 83 (closed squares) and control MAb 1 (closed circles). Each value represents the mean counts per 5 min of triplicate cultures.

Further it was investigated whether the panel of MAb could inhibit antigen-driven proliferation of H.243 T-cells. In this experiment, MAb were pre-incubated with T-cells and APC and three hours later, pulsed with different concentrations of peptide. FIG. 4 shows that TCR 64, TCR 70, TCR 76, TCR 78 and TCR 83 strongly inhibit antigen-driven proliferation. Up to 98% inhibition was observed with TCR 83. Dose response curves show that maximal inhibition could be obtained with as little as 100 ng/ml TCR 64, TCR 70 and TCR 83. TCR 78 was approximately tenfold less potent. The inhibition patterns were not dependent of whether suboptimal or saturating concentrations of peptide were added (results not shown). An anti-clonotype MAb directed against an other TCR (TCR 44) did not show any inhibition.

Figure 5:
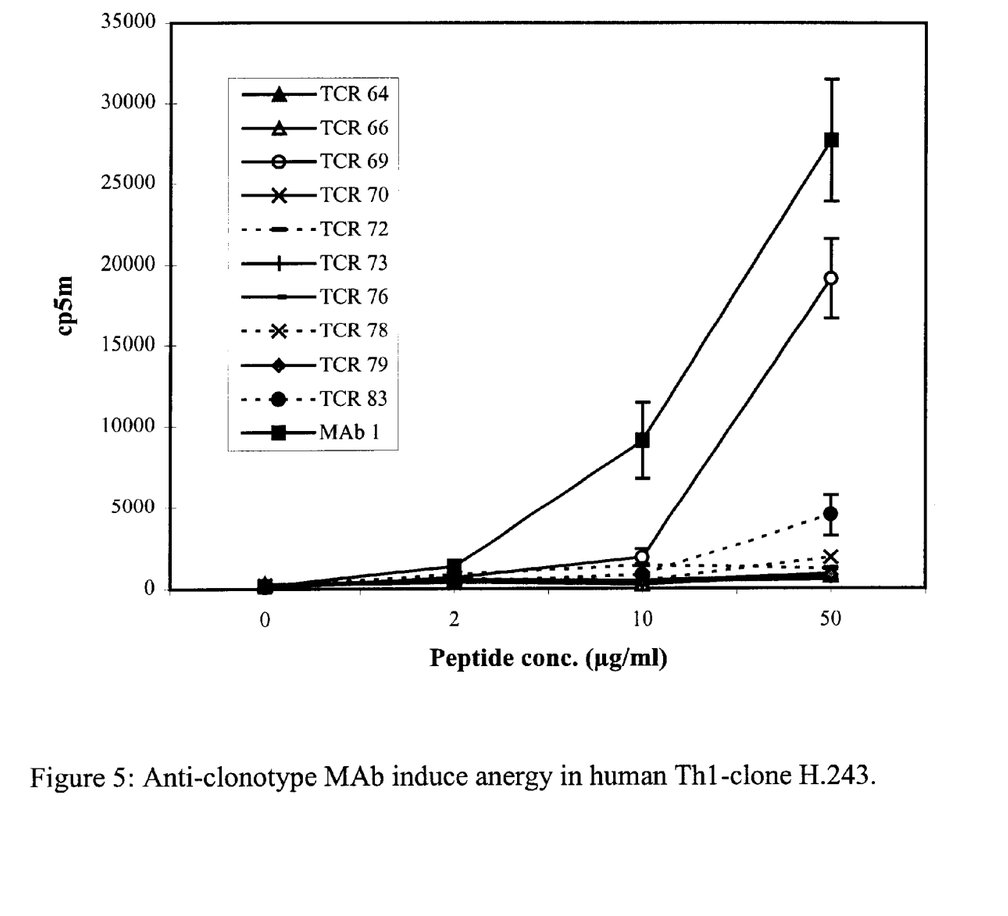
FIG. 5 Anti-clonotype MAb induce anergy in human Th1-clone H.243. Immobilized anti-clonotype MAb or control MAb 1 were incubated overnight with H.243 T cells. After removal of the cells from the anergic stimulus, the cells were given a full stimulus of increasing concentrations of peptide and DRB1*0401 matched APC. Proliferation was assessed by $^3$H-thymidine incorporation. Each value represents the mean counts per 5 min of triplicate cultures +/– standard deviation.

Anti-clonotype MAb Induce Unresponsiveness of Human T-cell Clone H.243 to Subsequent Stimulation with Antigen and APC T-cell receptor occupancy in the absence of costimulation is known to induce anergy. Previously we had found that immobilized anti-clonotype MAb to H.243 can functionally trigger the TCR of this clone. Therefore, it was interesting to investigate whether the same antibodies could induce anergy. For this purpose, 10 different anti-clonotype MAb were immobilized on 24-well plates and incubated overnight with H.243 T cells to give the anergic stimulus. Then, T cells were removed from the plates and it was tested whether they could respond to increasing concentrations of HC gp-39$^{262-277}$ (SEQ ID NO: 3) presented by irradiated, DRB1*0401-matched APC. FIG. 5 shows that this response was completely abrogated by 8 out of 10 MAb whereas H.243 cells incubated with control MAb 1 still responded well to peptide presented by APC. The response of T cells incubated with TCR 69 and TCR 83 was significantly reduced but not completely abrogated at higher peptide concentrations.

Anergic Cells Suppress the Response of Non-anergic Cells

Figure 6:
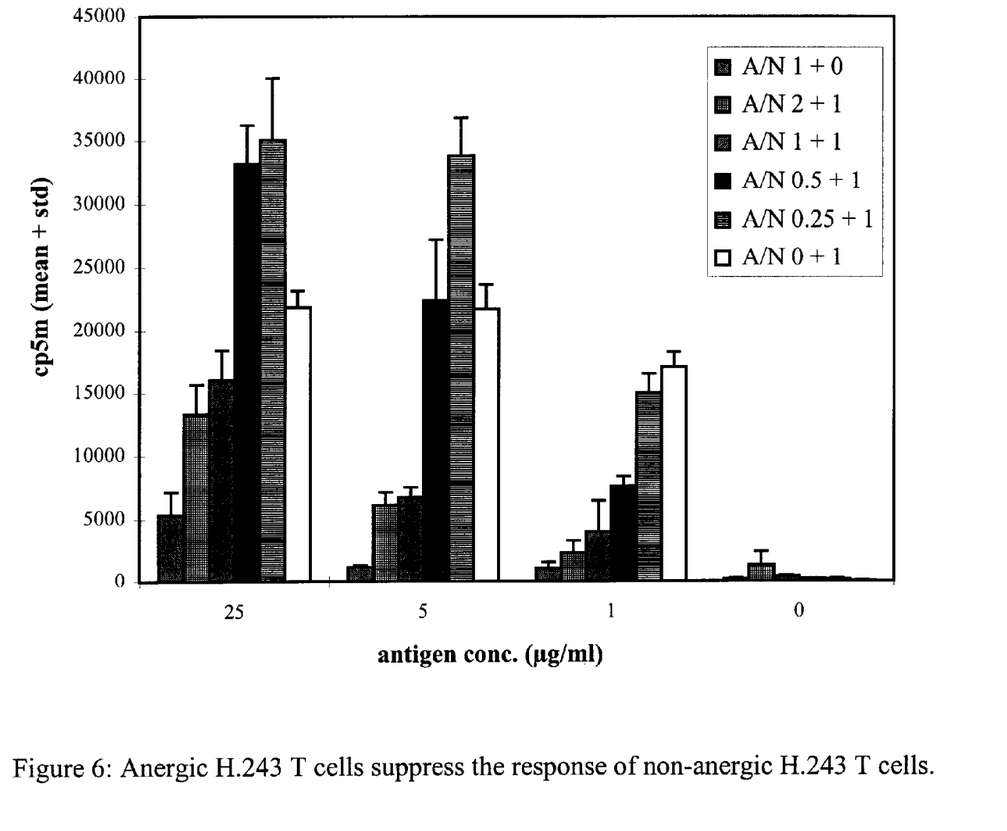
FIG. 6 Anergic H.243 T cells suppress the response of non-anergic H.243 T cells. Immobilized TCR 76 or control MAb 1 were incubated overnight with H.243 T cells. Then, both T-cell populations were used in a proliferation assay with increasing concentrations of peptide (or PHA) and APC using $2\times10^4$ T cells per well. in addition, variable amounts of anergic cells resulting from incubation with TCR 76 were mixed with $2\times10^4$ non-anergic cells resulting from incubation with Mab 1 and a proliferation assay was performed. A/N: ratio of anergic cells versus non-anergic cells; $1=2\times10^4$ cells. Proliferation was assessed by $^3$H-thymidine incorporation. Each value represents the mean counts per 5 min of triplicate cultures+standard deviation.

It was also investigated whether anergic H.243 cells were able to suppress the response of non-anergic H.243 cells. Anergy was induced with TCR 76 and non-anergic cells were obtained from incubation with control MAb 1. Subsequently, proliferation assays were performed with peptide HC gp-39$^{261-275}$ (SEQ ID NO: 2) using different T-cell populations viz. $2\times10^4$ anergic T cells per well, $2\times10^4$ non-anergic T cells per well or mixtures of decreasing concentrations of anergic T cells ($4\times10^4$, $2\times10^4$, $1\times104$ and $0.5\times10^4$) and $2\times10^4$ non-anergic T cells per well. The response of non-anergic cells was significantly reduced in a dose related fashion by the addition of anergic cells (FIG. 6). Approximately 90% reduction of proliferation was obtained at an antigen concentration of 1 μg/ml and a ratio anergic cells versus non-anergic cells of 2:1. At higher antigen concentrations less reduction of proliferation was observed (72% at 5 μg/ml and 39% at 25 μg/ml).

Thus this example shows that it is possible to generate anti-clonotype monoclonal antibodies against human T-cell receptors. This experiment resulted in ten hybridomas, four of which were deposited with the ECACC (Salisbury, UK), as indicated in Table III. The strategy did not require large numbers of T-cells or ample amounts of purified TCR. The method according to the invention is an attractive alternative for tedious recombinant procedures in which soluble TCR of TCR expressed on syngeneic mouse cells are generated to be used in immunization procedures. Thus also possible problems with conformational stability are avoided. As the monoclonal antibodies showed different responses in a test for antibody induced T-cell proliferation and a test for antibody mediated inhibition of antigen-driven T-cell proliferation (up to 98% inhibition was observed), this suggests that different epitopes are recognized on the same clonotypic structure.

If cross-linked all anti-clonotype monoclonal antibodies were able to induce proliferation of H.243 T-cells. It is demonstrated that small amounts of immobilized anti-clonotype MAb can induce anergy in the autoreactive clone. Following the anergic stimulus, T cells failed to proliferate upon restimulation as a result of a lack of IL-2 gene transcription. In addition, a diminished IFNg production was found. FACS analysis of the anergic cells indicated that anergy was not a result of TCR downmodulation or the absence of free TCR. In coculture experiments, anergic T cells were found to suppress the response of reactive cells from the same clone. This bystander suppression led to 90% inhibition of proliferation. The data demonstrate the energizing potential of clonotype-specific antibodies in vitro. Such MAb can be used for the induction and maintenance of antigen-specific T-cell tolerance in rheumatoid arthritis.

In sera of mice immunized by injecting rather pure TCR/CD3 immune complexes coupled to paramagnetic beads (Table I; immunization group IV). The sera of the mice tested more positive for the specific T-cell which was used for immunization than an irrelevant T-cell. However, it was not possible to obtain hybridomas producing anti-clonotype monoclonal antibodies. Even though in sera of mice immunized with small amounts of whole T-cells no specificity for the T-cell of interest versus an irrelevant T-cell could be demonstrated, the method according to the invention yielded hybridomas capable of producing anti-clonotype monoclonal antibodies.

It goes without saying that antigen binding fragments can be made of the monoclonal antibodies according to the invention, for example using papain. Also the monoclonal antibodies or antigen binding fragments thereof can be labelled to facilitate their detection and scope of the present invention encompasses all these forms.

It also goes without saying that the irrelevant cells used to remove non-specific B-cells, are preferably as much alike as the cell surface antigen-carrying cells.

TABLE I

Immunization schedules and characterization of sera

| Immun. group | antigen | adju-vant | route | agglutination /FACS | | proliferation induction | inhibition Ag-driven proliferation[#] | West. blot |
|---|---|---|---|---|---|---|---|---|
| | | | | T cell 1* (immun.) | T cell 2* (irrelevant) | | | |
| I | T cells | none | ip (5×) | +++ | +++ | – | ++ | – |
| II | T cells; TCR/CD3 | yes | ip; im; im; ip | +++ | +++ | – | ++ | – |
| III | TCR/CD3 | yes | ip; im; im; im; ip | – | – | +/– | – | – |
| IV | TCR/CD3 | yes | sc; sc; sc; ip | – | – | + | – | – |
| V | TCR/CD3 | none | is (5×) | + | +/– | + | – | – |
| | Normal Mouse Serum | | | – | – | – | – | – |

Groups of two BALB/C mice were immunized with either whole T cells or TCR/CD3 complexes bound to paramagnetic beads. Immunizations were performed in the absence or presence of adjuvant as indicated. Different routes of immunization were followed namely: ip = intraperitoneally; im = intramuscular; sc = subcuteneously; is = intrasplenic.
Sera from the mice were characterized for binding in a T-cell agglutination assay, FACS-staining and Western blot. Functional characterization was performed in an antibody-mediated T-cell proliferation assay and in a test for antibody-mediated inhibition of antigen-driven T-cell proliferation.
*T cell 1 = T-cell clone used for immunization; T cell 2 = irrelevant T-cell clone.
[#]+ means inhibition of T-cell proliferation.

TABLE II

Outgrowth of anti-T cell specific B cells in EL-4 B-cell cultures

| Number of wells inoculated | Plating density | Number of wells with B-cell outgrowth | Agglutination with H.243 | Agglutination with H.258 |
|---|---|---|---|---|
| 384 | x | 384 | 68 | 40 |
| 192 | 1/6 x | 171 | 13 | 7 |
| 192 | 1/36 x | 81 | 3 | 1 |

28 × 10⁶ lymphocytes were submitted to an immunobead selection procedure for the selection of anti-cloning specific B cells. The selected B cells were expanded at different plating densities in an EL-4 B-cell culture system and at day 8, supernatants were tested for agglutinating antibodies with the T cells of interest (H.243) and irrelevant T cells (H.258)
x: undetermined number of selected cells

TABLE III

Agglutination of different kinds of T cells with anti-TCR mAb

| mAb | isotype | T-cell agglutination with | | | |
|---|---|---|---|---|---|
| | | H.243[1] | 6 Vβ9 positive T cells | 2 Vα8 positive T cells | 8 other T cells |
| TCR 64 | IgG2a | + | − | − | − |
| TCR 66 | IgG1 | + | − | − | − |
| TCR 67 | n.d. | + | − | − | − |
| TCR 69 | IgG1 | + | − | − | − |
| TCR 70 | IgG2a | + | − | − | − |
| TCR 72 | IgM | + | − | − | − |
| TCR 73 | IgG1 | + | − | − | − |
| TCR 74 | n.d. | + | + | − | − |
| TCR 76 | IgG2a | + | − | − | − |
| TCR 78 | IgM | + | − | − | − |
| TCR 79 | IgG1 | + | − | − | − |
| TCR 83 | IgM | + | − | − | − |
| anti-Vβ9 | IgG2a | + | + | − | − |
| anti-αβ | IgG2b | + | + | + | + |
| control mAb | IgG1 | − | − | − | − |

[1] H.243: Vα8 en Vβ9 positive

LITERATURE

1. Moretta, A., et al. (1985) Selection and characterization of monoclonal antibodies to the idiotype-like structure of an interleukin-2-producing human leukaemia T-cell line. Int. J. Cancer 36: p. 253–259.
2. Oetgen, H. C. et al. (1986) A T3-like protein complex associated with the antigen receptor on murine T cells. Nature 320: p. 272–275.
3. Steenbakkers, P. G. A., et al. (1994) Efficient generation of monoclonal antibodies from preselected antigen-specific B cells. Molecular Biology Reports 19, p. 125–134.
4. Steenbakkers, P. G. A. et al (1992) A new approach to the generation of human and murine antibody producing hybridomas. J. Immunol. Methods 152, p. 69–77.
5. Laemmli, U. K. (1970) Cleavage of structural proteins during the assembly of the head of a bacteriophage T4. Nature 227: p. 680–685.
6. Towbin, H. et al. (1979) Electrophoretic transfer of proteins from polyacrylamide gels to nitrocellulose sheets: Procedure and some applications. Proc. Natl. Acad. Sci. USA 76: p. 4350–4354.

Abbreviations
PBS Phosphate Buffered Saline
BCIP 5-bromo-4-chloro-3-indoylphospate p-toluidine salt
NBT p-nitro blue tetrazolium chloride
BSA Bovine Serum Albumin
FCS Foetal Calf Serum
SAM Sheep anti Mouse
TSN T-cell supernatant
MAb monoclonal antibody (antibodies)
Manufacturers
Biorad, Richmond, Calif., U.S.A.
Gibco, Paisley, Scotland
Hyclone, Logan, U.S.A.
Packard, Meriden, Conn., U.S.A.

I claim:

1. A monoclonal antibody that specifically binds a clonotypic structure of a T-cell receptor associated with rhematoid arthritis, wherein the monoclonal antibody specifically binds the T-cell receptor of a human cartilage glycoprotein-39 (HC gp-39) reactive T-cell clone.

2. The monoclonal antibody of claim 1, wherein the T-cell clone is H.243 (ECACC accession No. 96103122).

3. The monoclonal antibody of claim 2, which is produced by a hybridoma selected from the group consisting of TCR 69 (ECACC accession No. 96103118), TCR 70 (ECACC accession No. 96103119), TCR 72 (ECACC accession No. 96103120) and TCR 83 (ECACC accession No. 96103121).

4. A pharmaceutical composition comprising the monoclonal antibody of claim 1 admixed with a suitable excipient, suitable for the treatment of rheumatoid arthritis.

5. A pharmaceutical composition comprising the monoclonal antibody of claim 2 admixed with a suitable excipient, suitable for the treatment of rheumatoid arthritis.

6. A pharmaceutical composition comprising the monoclonal antibody of claim 3 admixed with a suitable excipient, suitable for the treatment of rheumatoid arthritis.

7. A diagnostic reagent comprising the monoclonal antibody of claim 1.

8. A diagnostic reagent comprising the monoclonal antibody of claim 2.

9. A diagnostic reagent comprising the monoclonal antibody of claim 3.

\* \* \* \* \*

```
                       SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 1:

Arg Ser Phe Thr Leu Ala Ser Ser Glu Thr Gly Val Gly
1               5                   10

(2) INFORMATION FOR SEQ ID NO: 2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:
```

-continued

```
Phe Gly Arg Ser Phe Thr Leu Ala Ser Ser Glu Thr Gly Val Gly
1               5                   10                  15
```

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: single
        (D) TOPOLOGY: linear     (ii) MOLECULE TYPE: protein     (v) FRAGMENT TYPE: internal     (xi) SEQUENCE DESCRIPTION: SEQ ID NO: 3:

```
Gly Arg Ser Phe Thr Leu Ala Ser Ser Glu Thr Gly Val Gly Ala Pro
1               5                   10                  15
```